United States Patent [19]

Rislove

[11] Patent Number: 4,791,065

[45] Date of Patent: Dec. 13, 1988

[54] ETHANOL SENSITIVE SOLID

[75] Inventor: David J. Rislove, Winona, Minn.

[73] Assignee: Grobel Research Corporation, Orlando, Fla.

[21] Appl. No.: 839,230

[22] Filed: Mar. 13, 1986

[51] Int. Cl.$^4$ .................... G01N 31/22; G01N 33/497
[52] U.S. Cl. .................................... 436/132; 436/166; 436/900; 422/56; 422/85
[58] Field of Search ............... 436/132, 900, 166; 422/56, 57, 84, 85

[56] References Cited

U.S. PATENT DOCUMENTS

| | | | |
|---|---|---|---|
| Re. 27,008 | 12/1970 | Luckey | 436/900 X |
| 2,939,768 | 6/1960 | Grosskopf | 436/900 X |
| 3,208,827 | 9/1965 | Borkenstein | 436/900 X |
| 3,223,488 | 12/1965 | Luckey | 436/900 X |
| 3,238,783 | 3/1966 | Wright | 73/863.01 |
| 3,303,840 | 2/1967 | Etzlinger | 128/719 |
| 3,437,449 | 4/1969 | Luckey | 436/900 X |
| 3,455,654 | 7/1969 | McConnaughey | 436/132 |
| 3,544,273 | 12/1970 | McConnaughey | 422/85 |
| 3,552,930 | 1/1971 | Borkenstein | 436/900 X |
| 3,582,274 | 6/1971 | Keyes | 436/900 X |
| 3,607,095 | 9/1971 | Etzlinger | 436/900 X |
| 3,618,393 | 11/1971 | Principe et al. | 73/864.52 |
| 3,684,456 | 8/1972 | McConnaughey | 422/56 X |
| 3,951,855 | 4/1976 | Principe et al. | 436/9 |
| 4,080,170 | 3/1978 | Borkenstein | 436/900 X |
| 4,294,583 | 10/1981 | Leichnitz | 436/135 |
| 4,353,869 | 10/1982 | Guth | 422/102 |

FOREIGN PATENT DOCUMENTS

| | | | |
|---|---|---|---|
| 1489484 | 7/1967 | France | 436/900 |
| 2450454 | 9/1980 | France | 436/900 |

OTHER PUBLICATIONS

Be Sure TM 10-Second Breath Alcohol Test Device Package, Viking Industries, Inc., Medpro Division.

*Primary Examiner*—Benoit Castel
*Assistant Examiner*—Jill Johnston
*Attorney, Agent, or Firm*—Arnold, White & Durkee

[57] ABSTRACT

This invention is an ethanol sensitive solid useful for the colorimetric determination of ethyl alcohol in human breath samples. The solid is prepared by wetting silica gel with an acidic solution of a chromium(VI) salt and then heating to substantially dehydrate the material. The solid so prepared will change color from a deep orange to blue-green in the presence of alcohol. By packing the solid into a transparent tube and passing a known volume of breath sample through it, the blood alcohol content of the user may be estimated by measuring the color-changed portion of the packed tube.

8 Claims, No Drawings

ETHANOL SENSITIVE SOLID

BACKGROUND OF THE INVENTION

1. Field of the Invention

This invention relates to the colorimetric determination of ethyl alcohol in human breath samples. More specifically, the invention is a solid substance which changes color when exposed to a gas containing ethanol vapor.

2. Description of the Related Art

It is widely recognized that blood alcohol content may be directly correlated to the alcohol concentration of a person's alveolar breath. Law enforcement agencies commonly rely on this relationship to determine the blood alcohol content (BAC) of a suspect by using the well-known "Breathalyzer." This device is an apparatus for analyzing the alcohol content of human breath. In operation, a 50-mL sample of breath is collected in a heated reservoir and is then bubbled through an ampoule containing a dilute solution of potassium dichromate in 50% sulfuric acid. The reduction of the dichromate by alcohol in the breath sample is accompanied by a color change in the acid dichromate reagent. This color change is measured photometrically. Although the apparatus is sufficiently accurate for practical purposes, it is relatively complex, expensive, and the liquid reagent employed is highly corrosive and great care must be taken in handling the ampoules and in disposing of them after use. All these factors militate against its use except by well-trained operators under controlled conditions. This is unfortunate, since a need exists for a reliable, accurate, simple and inexpensive BAC device which could be used by motorists and other members of the general public.

In addition to the "Breathalyzer," a number of other devices exist for estimating BAC based on the color change produced when ethanol is oxidized by hexavalent chromium compounds under acidic conditions. Generally speaking, the color change is from yellow to blue-green or violet, reflecting a change from chromate ions to chromic ions. With respect to general chromium ion chemistry, chromic ions ($CR^{+3}$) usually exist in a pH-dependent equilibrium with chromite ions ($CrO_2^-$) while dichromates ($Cr_2O_7^=$) exist in a pH-dependent equilibrium with chromates ($CrO_4^=$). Chromates are yellow; dichromates are orange. Chromic acid ($H_2CRO_4$), the hydrate of $CrO_3$, exists only in solution or as chromate salts. In an acid solution, a redox reaction will result in $Cr_2O_7^=$ (orange) being reduced to $Cr+3$ (green or blue-green).

In some instances, silica gel has been used as a support for the acid chromate. This provides a solid phase reagent system which reduces the hazard associated with handling solutions in strong, concentrated acids. An example of a device employing this system is the Kitagawa tube, which is described in Wright, U.S. Pat. No. 3,238,783, as consisting of a narrow-bore glass tube containing powdered silica as a carrier for the reagent. The reagent is described as an anhydrous form of chromic acid which is normally yellow but changes to bluish-grey upon reduction by alcohol. It is further said that in such a tube, the length of the stain gives a measure of the quantity of alcohol passed through it.

Etzlinger, U.S. Pat. No. 3,303,840, describes an apparatus which uses a similar tube for estimating BAC from a breath sample. After collection, the breath sample is forced through a tester tube containing potassium dichromate. During this passage, the alcohol contained in the gas reduces the yellow dichromate to a greenish chromium-containing product. The location along the tube of the separation between the yellow part and the greenish part of the contents of the testing tube is compared against a graduated scale to read the alcohol content in the blood of the person providing the breath sample.

McConnaughey, U.S. Pat. No. 3,544,273, describes still another sampling device for obtaining alveolar breath samples. The collected sample is analyzed for alcohol by discharging it through a colorimetric detector tube which is said to be a glass tube containing a bed of reagent that changes color in response to contact with the alcohol in the sample. When the sample is passed through the tube "a color change occurs lengthwise of the bed, the length of the color-changed portion being dependent on the amount of detectable gas in the sample." An especially suitable indicator is said to be disclosed in U.S. Pat. No. 3,455,654 in which a hexavalent chromium compound and a pentavalent phosphoric acid are supported on an inert carrier. This indicator is said to change color from yellow to dark green on reaction with ethyl alcohol. A typical illustrative formulation contains 0.53 gram of chromium trioxide and 1.67 grams of metaphosphoric acid carried on 100 mL of 8–14 mesh silica gel.

As noted earlier, it is a common shortcoming of the above-described BAC devices and systems that they involve color changes which are not always easy to perceive. Clear and ready perception is important since the devices and systems depend in large measure upon the visual distinctiveness of a line of demarcation between reacted and unreacted portions of reagent within a tube. The color change produced in many of these devices and systems is from yellow to greenish-blue. Such a change is not always easy to perceive, especially by relatively unskilled personnel under less-than-optimum lighting conditions. There exists a clear need for a BAC system which is reliable, easy to use and relatively inexpensive.

SUMMARY OF THE INVENTION

The present invention comprises an ethanol sensitive solid detection system which produces a particularly distinct color change upon exposure to a gas containing ethyl alcohol vapor. The invention has special utility in apparatus for estimating the blood alcohol content of a person. In a preferred embodiment a breath sample is forced through a transparent tube packed with the solid. The presence of alcohol will cause the solid to change color rapidly and very distinctively from deep orange to blue-green. If the volume of the breath sample is known, the BAC of the person involved may be determined from the length of the color-changed portion of the solid system in the detector tube.

The ethanol sensitive system of the invention is prepared by first adding a solution of potassium dichromate in sulfuric acid to a solid carrier such as silica gel. The amount of solution added to the gel is preferably sufficient to wet the particles of gel uniformly with little or no lumping. The wetted gel is then heated while being agitated to remove water from the gel and until the color of the gel changes from yellow to a deep orange—i.e., orange-red. Preferably, the heating is continued until a dense white gas forms and is expelled from the gel. It appears that the gas is sulfur trioxide derived from the sulfuric acid. The resulting gel is then cooled and preferably maintained in a dry environment. The product is a homogeneous deep orange and comprises, in general, a dehydrated mixture of chromium(VI) and sulfate groups.

It is contemplated that the above-described compositions are applicable for use in various BAC devices. Preferably, the compositions are installed in transparent glass tubes, ampoules, or the like and sealed from the atmosphere, pending use. In use, a person whose breath is to be analyzed, blows a metered quantity of breath through the tube or other container containing the composition. Alcohol contained in the breath reacts with the chromium(VI) components in their acidic environment to effect a color change. Depending on the amount of alcohol present, the new color (blue, blue-green, or the like) will extend downstream in the tube a distance which is a function of the amount of alcohol present.

The compositions described may be varied considerably without departing from the principles and scope of the invention. In a general aspect, the compositions comprise chromium(VI) ions deposited on a solid carrier in an acid environment, and which have been dehydrated by heating to a deep orange color. When the acid is sulfuric acid, the heating is continued until white vapors are released. The vapors are considered to be sulfur trioxide. It is contemplated that carriers other than silica gel may readily be used in the practice of the invention. For example, other carriers considered suitable are alumina and magnesia.

It is also contemplated that chromium compounds other than potassium dichromate may be used. Other chromium compounds deemed suitable include chromium trioxide, pyridinium chlorochromate (or pyridinium dichromate), and sodium dichromate.

Acids other than sulfuric which may be used to practice this invention include phosphoric acid, polyphosphoric acid, methanesulfonic acid and para-toluenesulfonic acid.

DESCRIPTION OF THE PREFERRED EMBODIMENT

An ethanol sensitive solid may be prepared as follows:
1. Weigh 5 grams of silica gel (Davisil brand, Aldrich Chemical Co., grade 636, 35–60 mesh) into a 125-mL Erlenmeyer flask;
2. Prepare an acidic dichromate solution as follows:
   a. Place 0.5 gram of analytical reagent grade $K_2Cr_2O_7$ in a 125-mL Erlenmeyer flask;
   b. Add 10 mL of 3 molar aqueous $H_2SO_4$ and 10 mL deionized $H_2O$;
   c. Heat the mixture gently on a steam bath until the crystals of $K_2Cr_2O_7$ are completely dissolved;
   d. Cool the resulting solution to room temperature.
3. Add 4 mL of the acidic dichromate solution to the flask containing the silica gel;
4. Mix the acidic dichromate solution with the silica gel until all the silica gel crystals are wetted and no lumps are visible;
5. Gently heat the resulting mixture over the open flame of a Bunsen burner with constant shaking while simultaneously heating the upper portion of the flask to expel condensed water;
6. Continue heating and shaking the flask containing the dichromate-silica gel mixture for approximately three minutes until the mixture changes color from yellow to orange-red and a dense white gas fills the flask;
7. Discontinue the heating; allow the solid to cool; and place it in a sealed container. The crystals of the solid should be homogeneously colored a deep orange.

The ethanol sensitive solid may be used for estimating a person's blood alcohol content by packing approximately 100 mg of it into a 5-cm length of 4-mm i.d. glass tubing plugged with cotton or glass wool and a 2-mm section of silic gel. A micro-spatula may be used to transfer the solid from its storage container to the tube. The tube may be gently tapped on a hard surface between spatula loads to pack the ethanol sensitive solid into the tube. Insert more silica gel (approximately 2 mm) and another cotton or glass wool plug (approximately 5 mg) to hold the packed solid in the center section of the tube. The resulting tester will contain a 10-mm column of the orange ethanol sensitive solid between two plugs of silica gel and cotton (or glass wool) in a glass tube.

An 800-mL breath sample is passed through the tester in a period of one minute. If the person supplying the breath sample has a BAC of more than about 0.02% but less than about 0.3%, his BAC may be estimated by measuring the length of the ethanol sensitive solid which has changed color from deep orange to blue-green and comparing this length to similarly measured lengths from subjects with known BAC's over the range of interest. Alternatively, a graduated scale may be prepared from which the BAC may be interpolated by placing the tester alongside the scale and noting the position of the demarcation between the color-changed and noncolor-changed portions of the ethanol sensitive solid. Such a scale may be prepared by obtaining breath samples from subjects with known BAC's covering the range of interest, passing the same volume of such samples through similarly prepared testers at the same flow rate, and marking the demarcation line positions on the scale.

It will be apparent to those skilled in the art that the dynamic range of such testers may be altered by varying either the length or the diameter of the packed portion of the tube. The longer the portion, the higher the values of BAC's that may be estimated; the more narrow the portion, the lower the limit of determination.

What is claimed is:

1. An ethanol sensitive solid which changes color upon exposure to ethanol prepared by the process consisting essentially of the steps of wetting particles of silica gel with a solution comprising a hexavalent chromium compound and sulfuric acid, heating the wetted particles until dense white fumes are evolved and cooling the particles to thereby obtain said ethanol sensitive solid.

2. The solid defined in claim 1 in which the chromium compound is an alkali metal dichromate.

3. The solid defined in claim 1 in which the chromium compound is potassium dichromate.

4. An ethanol sensitive solid consisting essentially of a solid particulate carrier having absorbed thereon a substantially dehydrated mixture of a hexavalent chromium compound and an acid sulfate compound, said carrier being substantially chemically inert toward said mixture.

5. The composition defined in claim 4 which is a deep orange in color.

6. A method of making an ethanol sensitive solid which consists essentially of:

wetting silica gel particles with an acid solution of a hexavalent chromium compound;

heating the wetted gel sufficiently to drive off substantially all free water and cooling the gel to thereby obtain said ethanol sensitive solid.

7. The method defined in claim 6 in which the chromium compound is potassium dichromate and the acid is sulfuric acid.

8. An ethanol sensitive solid which changes color upon exposure to ethanol, prepared by the process consisting essentially of the steps of wetting a solution comprising a hexavalent chromium compound and sulfuric acid onto silica gel, heating until water vapor and dense, white fumes of sulfur trioxide are evolved and cooling the gel to thereby obtain said ethanol sensitive solid.

* * * * *